United States Patent [19]

Jeppesen et al.

[11] 4,064,609
[45] Dec. 27, 1977

[54] MEMBRANE MOUNTING DEVICE

[75] Inventors: Borge Jeppesen, Glostrup; Flemming Aas, Soborg, both of Denmark

[73] Assignee: Radiometer A/S, Denmark

[21] Appl. No.: 733,893

[22] Filed: Oct. 19, 1976

[30] Foreign Application Priority Data

Oct. 20, 1975   Denmark ............................. 4709/75

[51] Int. Cl.² ........................................... B23P 19/02
[52] U.S. Cl. ....................................... 29/235; 29/448
[58] Field of Search .......................... 29/235, 448, 450

[56] References Cited

U.S. PATENT DOCUMENTS

| 3,289,286 | 12/1966 | Belanger | 29/235 |
| 3,347,083 | 10/1967 | Turpin et al. | 29/235 |
| 3,623,211 | 11/1971 | Zuhlke | 29/448 |

Primary Examiner—James L. Jones, Jr.
Attorney, Agent, or Firm—Robert E. Burns; Emmanuel J. Lobato; Bruce L. Adams

[57] ABSTRACT

The invention relates to a membrane mounting device for mounting a membrane or foil in a stretched condition at one end of a rod-shaped or tubular member, such as a measuring electrode member. The mounting device comprises a membrane to be mounted as well as a resilient mounting ring for retaining the membrane in its mounted condition. The resilient mounting ring is preferably kept in a condition substantially free from tension. However, immediately before use of the mounting device the ring may be tensed or stretched, and one end of a rod-shaped or tubular member may then be inserted in the membrane mounting device whereby the membrane may automatically be mounted at the said end of the rod-shaped or tubular member.

6 Claims, 5 Drawing Figures

MEMBRANE MOUNTING DEVICE

BACKGROUND OF THE INVENTION

1. Field of the Invention

Various type of electrochemical measuring electrodes are at one end provided with a gas permeable membrane which is retained in position by means of an elastic or resilient ring surrounding said end of the measuring electrode. As the user of such measuring electrodes has to mount and/or replace the membranes on the measuring electrodes from time to time it is important that the membranes may be mounted in a manner which is not only simple, but also secures a correct and reproduceable mounting.

The present invention relates to a mounting device for mounting a membrane or foil in a stretched condition at one end of a measuring electrode member or a similar rod-shaped or tubular member.

2. Description of the Prior Art

Austrian Patent Specification No. 284,328 discloses a device or tool for mounting membranes on measuring electrodes. This known tool comprises a body member or base member having a throughgoing passage defining an upwardly facing shoulder. When a membrane has to be mounted by means of a resilient or elastic ring the user must first place the ring on a cylindrical mandrel having a conical tip. The user places the ring around the conical tip and moves it manually onto the cylindrical part of the mandrel, whereby the ring is being resiliently stretched. Thereafter, the user inserts the mandrel on which the ring is placed into the passage formed in the base member or body member till the ring abuts the upwardly directed shoulder therein. The user now has to place a membrane on the upper side of the base member and thereafter a heavy retaining ring on the upper side of the membrane whereby the rim portion of the membrane is being clamped between the upper side of the base member and the lower side of the retaining ring. When the mounting tool has been made ready as described the user inserts the end portion of an electrode on which the membrane should be mounted, in the retaining ring and pushes the electrode towards the membrane which will thereby be wrapped around the electrode end portion, the rim portion of the membrane being pulled out from its position between the retaining ring and the base member. During the continued downward movement of the electrode end portion through the passage in the base member, the electrode end portion with the membrane wrapped therearound engages with the upper free end of the cylindrical part of the mandrel and pushes the mandrel downwardly in the tool passage. Thereby the stretched resilient ring abutting the upwardly directed shoulder will be slipped off the mandrel and moved to a position around the electrode end portion having an outer diameter equal to or somewhat smaller than the outer diameter of the cylindrical part of the mandrel.

Even though use of the known tool described above somewhat facilitates the mounting operation compared with mounting procedures previously used, it would be desirable to make the membrane mounting procedure still more simple for the user and thereby further to reduce the risk of erroneous mounting.

SUMMARY OF THE INVENTION

The present invention provides a mounting device for mounting a membrane or a foil in a stretched condition at one end of a rod-shaped or tubular member, such as a measuring electrode member, said mounting device comprising a body member defining a passage therein and having first and second abutment surfaces at opposite first and second ends of said passage, respectively, a membrane or foil arranged at said first end of the passage and extending transversely in relation thereto, said membrane being releasably retained at its rim portion, a ring stretching means including a radially enlarged part which is positioned at said second end of the passage and which may engage with said second abutment surface, and a part extending axially from said enlarged part through said passage, said ring stretching means being axially displaceable in relation to said body member, and a separate resilient mounting ring surrounding the axially extending part of the said stretching means and positioned at said first end of the passage, the outer diameter of the said ring exceeding the minimum diameter of the adjacent first end of said passage, whereby said ring may engage with said first abutment surface.

In the mounting device according to the invention inadvertent axial movement of the ring stretching means or mandrel is limited by said radially enlarged part and by the resilient mounting ring of which the latter serves as a releasable locking member. Consequently, the manufacturer and/or distributor of measuring electrodes of the type mentioned above may supply the membrane mounting device with the resilient ring and preferably also the membrane positioned in the mounting device ready for use. When a new membrane should be mounted on a measuring electrode the user may effect the mounting simply by inserting the end of the electrode in the mounting device and by relatively displacing the electrode and/or parts of the mounting device. The mounting device according to the invention is preferably of the disposable type. As mentioned above, the resilient ring serves as a releasable locking member retaining the ring stretching means or mandrel in position. Therefore, the mounting device may be of such a structure that the stretching means or mandrel is separated from the body member when the resilient mounting ring has been removed from the stretching means or mandrel by use of the mounting device. Thus, it is clearly indicated when a device has been used and should be disposed.

If the resilient mounting ring is kept stretched or tensed for a longer period of time, for example in the period of time in which the mounting device is stored before, use the ring may partly lose its elasticity or resiliency. In order to avoid such loss of elasticity, according to the invention said axially extending part may have a diverging free end portion extending beyond said abutment surface, said mounting ring being positioned spaced from the free end of said portion in a substantially strainless condition.

According to the invention the membrane mounting device may comprise a tubular or annular holding means holding said membrane, said holding means being mounted so as to be movable in axial direction in relation to said body member and towards said first abutment surface, and means for transferring at least part of this movement to said ring stretching means, whereby the resilient mounting ring may be moved to a position close to the free end of said diverging free end portion and transferred to a stretched condition. When a membrane should be mounted by means of such an embodiment, the user must first push the membrane holding means axially inwardly whereby also the ring stretching means or mandrel is moved axially so as to stretch the mounting ring and position it close to the free end of the mandrel. The user may now push the end of the electrode into the mounting device whereby the membrane is being mounted in the manner described above.

The common axial displacement of the membrane holding means and the ring stretching means or mandrel may be obtained by transferring means comprising at least one elongated member positioned radially outside said passage and extending axially between said holding means and said stretching means and being connected to only one of these means, said membrane being positioned adjacent to or closely spaced from the free end of said diverging end portion. Thus, the mutual positions of the membrane holding means and the ring stretching means are substantially maintained during the common displacement of these means.

The said holding means may comprise a tubular portion extending axially outwardly from said membrane for receiving and guiding the rod-shaped or tubular member on which the membrane is to be mounted. Thus, the membrane holding means also comprises a surface for guiding the rod-shaped member or electrode member when it is pushed into the mounting device whereby the risk of erroneous mounting of the membrane is considerably reduced.

The rim portion of the membrane or foil may be releasably retained in the mounting device or holding means in any suitable manner. It is preferred, however, that the foil is releasably retained by frictional engagement.

BRIEF DESCRIPTION OF THE DRAWINGS

The invention will now be further described with reference to the drawings showing an embodiment of the mounting device or mounting tool according to the invention, and wherein.

DESCRIPTION OF THE PREFERRED EMBODIMENT

Figure 5:
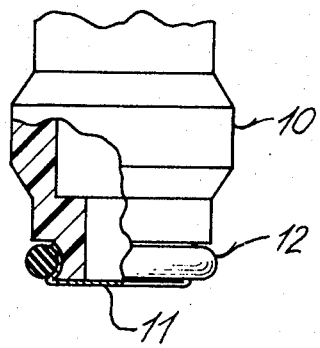
FIG. 5 is a side view and partially sectional view of the electrode end portion in an enlarged scale and with a membrane mounted thereon.

FIG. 5 shows an end portion of an electrode member 10 having a membrane 11 extended over its end. The rim portion of the membrane is retained by means of a resilient or elastic ring or O-ring 12 surrounding the free end of the electrode member 10 and positioned in a channel or groove formed in the outer surface thereof. From time to time the membrane 11 must be replaced by a new membrane. The used membrane may easily be peeled off when the ring 12 has been removed, and the new membrane may be mounted in a simple manner by means of a mounting tool or mounting device as that shown in FIGS. 1 - 4.

This mounting device is adapted to be used one time only and when it is supplied to the user it contains the membrane 11 as well as the elastic ring 12. The embodiment shown on the drawings comprises three separate main parts, namely a body member or base member 13, a ring-extending member or mandrel member 14, and a membrane holder 15. The base member 13 has the form to a tube with an inner transverse wall 16 defining a throughgoing axial passage 17 therein and a substantially radially directed abutment surface or shoulder 18.

The mandrel member 14 comprises an enlarging mandrel extending through the axial passage 17 and having a substantially cylindrical end portion 19, a substantially frustoconical ring-extending or ring-enlarging part 20, a radially enlarged part 21, and a neck portion 22 interconnecting the ring-extending part 20 and the radially enlarged part 21. Two column-like supporting elements 23 extending axially in the same direction as the enlarging mandrel and through holes defined in the transverse wall 16, and the length of these supporting elements are substantially the same as that of the enlarging mandrel.

Figure 1:
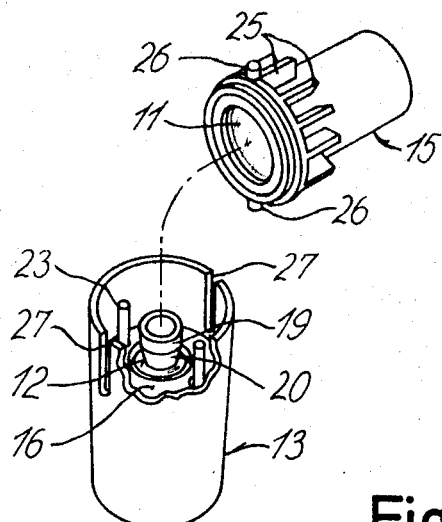
FIG. 1 is a perspective exploded view of the mounting device, a wall part having been cut away.
Figure 2:
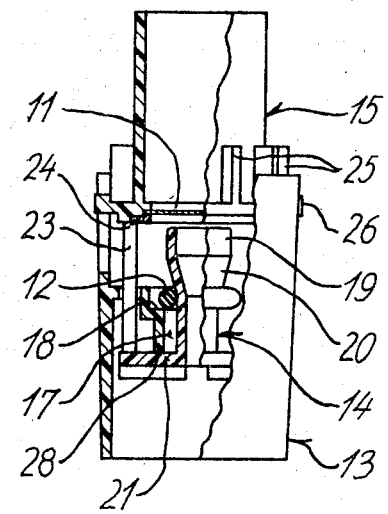
FIG. 2 is a side view and partially sectional view of the mounting device.
Figure 4:
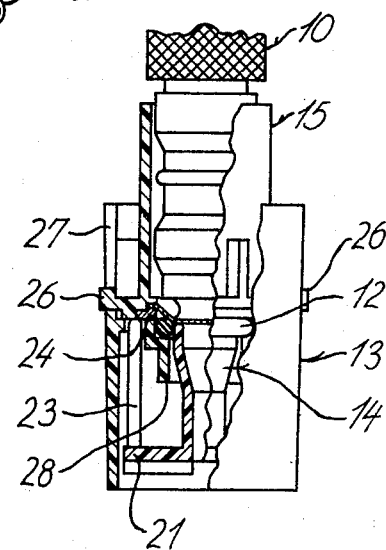
FIG. 4 is a view corresponding to that of FIG. 3, the membrane mounting ring having been moved to an inward position adjacent to the outer end of the stretching mandrel.

The membrane holder 15 is formed as a tube, and the membrane 11 is extended transversely at one end of the tube by means of a retainer ring 24, the rim of the membrane being clamped between that ring and an inner shoulder formed in the holder 15. The outer surface of the end portion of the membrane holder carrying the membrane 11 is provided with a plurality of radially extending ribs 25, and the radial outer edges of these ribs define a cylinder surface having a diameter corresponding substantially to the inner diameter of the base member 13. Furthermore, the said end portion of the membrane holder has two radially extending, diametrically oppositely arranged studs or pins 26. As indicated in FIG. 1, the membrane holder 15 may be inserted in the base member 13, the studs 26 being received in corresponding axial slots or slits 27 which prevent rotation of the membrane holder 15 in relation to the base member 13, but allow axial displacement of these members in relation to each other. The width of the slots 27 is preferably slightly less than the diameter of the studs 26 so that the studs are received in the slots with a tight frictional fit. However, at two axially spaced positions of the studs 26, corresponding for example to the relative positions of the base member 13 and the membrane holder 15 as shown in FIGS. 2 and 4, respectively, the slots 27 may have an enlarged width in order to clearly indicate these positions. The ribs 25 serve as guiding members for guiding the membrane holder when it is displaced in the base member 13. The friction engagement or tight fit between the studs 26 and the corresponding slots or slits 27 secures that the membrane holder 15 is not inadvertently separated from the base member 13.

The membrane mounting device shown on the drawings may be supplied to the user with the parts in the relative position shown in FIG. 2, namely with the membrane 11 mounted in the membrane holder 15 and the resilient ring 12 positioned around the enlarging mandrel. The relative dimensions of the axial passage 17 formed in the base member 13 and of the mandrel member 14 are preferably chosen so that the radially enlarged part 21 of the mandrel member engages an adjacent end surface 28 of the a tubular protrusion formed on the transverse wall 16 and encircling the axial passage 17, when the ring 12 is positioned around the enlarging mandrel at the transition between the neck portion 22 and the ring-enlarging part 20 and simultaneously engages the radial abutment or shoulder 18. The resilient ring 12 which is in a substantially non-stretched, strainless condition in that position, will then serve as a locking element or locking member retaining the mandrel member 14 within the base member 13 in that axial position. In the starting position of the mounting device shown in FIG. 2 the membrane holder 15 engages the free end of the supporting elements 23, and the membrane 11 is then arranged closely axially spaced from the free end of the cylindrical end portion 19 of the enlarging mandrel.

Figure 3:
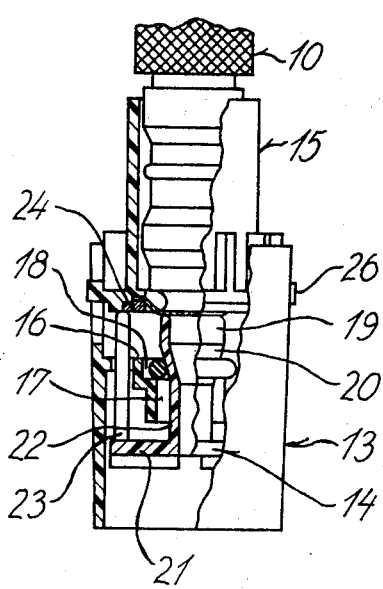
FIG. 3 is a view corresponding to that of FIG. 2, but an electrode end portion on which a membrane is to be mounted, has been inserted in the mounting device.

When a membrane is to be mounted on an electrode member 10 the user first pushes the membrane holder 15 inwardly into the base member 13. The axial force exerted on the membrane holder 15 will then via the supporting elements 23 be transferred to the mandrel member 14 which will then be axially displaced in relation to the base member 13 together with the membrane holder 15. The shoulder 18 prevents the resilient ring 12 from taking part in that axial displacement and, consequently, as illustrated in FIG. 3 the ring is moved along the ring-enlarging part 20 of the mandrel whereby the ring is extended or enlarged. When the membrane holder 15 has been pushed so far into the base member 13 that the stud 26 has reached the bottom of the slots 27 the membrane holder cannot be pushed further into the base member. That position in which the ring 12 has been moved right out to the outer end of the cylindrical end portion 19 of the enlarging mandrel is shown in FIG. 4. The user now inserts the electrode member 10 in the tubular membrane holder and pushes the electrode member inwardly towards the membrane 11, whereby the membrane is clamped between the adjacent ends of the electrode member 10 and of the mandrel, respectively. A further inwardly directed axial displacement of the electrode member 10 will cause that the rim of the membrane is pulled free from its frictional engagement with the membrane holder, and the extended elastic ring will slide from the cylindrical mandrel portion 19 till a position around the electrode member 10 where it will retain the membrane 11 in a stretched condition as shown in FIG. 5. The mandrel member 14 will now be released and separated from the base member 13, whereby it is indicated that the mounting device has been used and may be discarded.

It should be noted that the mutual axial displacement of the membrane holder 15 and the base member 13 from the relative positions shown in FIG. 2 to those shown in FIG. 4 may be made immediately before the electrode member 10 is inserted in the membrane holder 15, if desired. Alternatively, the said displacement may be made while the electrode member 10 is arranged in the base member 15 as shown in FIG. 3.

It should be understood that several amendments and modifications of the embodiment described above could be made within the scope of the present invention. It should also be noted that even though the present invention has primarily been described in connection with mounting of a membrane on an electrode member, the principles of the present invention may also be used in other cases where a membrane or foil should be mounted on another type of a rod-shaped or tubular member stretched over an end surface thereof.

We claim:

1. A mounting device for mounting a membrane or a foil in a stretched condition at one end of a rod-shaped or tubular member, such as a measuring electrode member, said mounting device comprising
    a body member defining a passage therein and having first and second abutment surfaces at opposite first and second ends of said passage, respectively,
    a membrane or foil arranged at said first end of the passage and extending transversely in relation thereto, said membrane being releasably retained at its rim portion,
    a ring-stretching means including a radially enlarged part which is positioned at said second end of the passage and which may engage with said second abutment surface, and a part extending axially from said enlarged part through said passage, said ring-stretching means being axially displaceable in relation to said body member, and
    a separate resilient mounting ring surrounding the axially extending part of said stretching means and positioned at said first end of the passage, the outer diameter of said ring exceeding the minimum diameter of the adjacent first end of said passage, whereby said ring may engage with said first abutment surface.

2. A mounting device according to claim 1, wherein said axially extending part has a diverging free end portion extending beyond said first abutment surface, said mounting ring being positioned spaced from the free end of said end portion in a substantially strainless condition.

3. A mounting device according to claim 2, further comprising a tubular or annular holding means holding said membrane, said holding means being mounted so as to be movable in axial direction in relation to said body member and towards said first abutment surface, and means for transferring at least part of this movement to said ring-stretching means, whereby the resilient mounting ring may be moved to a position close to the free end of said diverging free end portion thereby transferred to a stretched condition.

4. A mounting device according to claim 3, wherein said transferring means comprise at least one elongated member positioned radially outside said passage and extending axially between said holding means and said stretching means and being connected to only one of these means, said membrane being positioned adjacent to or closely spaced from the free end of said diverging end portion.

5. A mounting device according to claim 3, wherein said holding means comprises a tubular portion extending axially outwardly from said membrane for receiving and guiding the rod-shaped or tubular member on which the membrane is to be mounted.

6. A mounting device according to claim 2, wherein the rim portion of the membrane or foil is releasably retained by frictional engagement.

* * * * *